United States Patent [19]
Micheels et al.

[11] Patent Number: 5,957,858
[45] Date of Patent: Sep. 28, 1999

[54] SYSTEMS AND METHODS FOR MONITORING RELATIVE CONCENTRATIONS OF DIFFERENT ISOTOPIC FORMS OF A CHEMICAL SPECIES

[75] Inventors: Ronald H. Micheels, Concord, Mass.; Jonathan D. Kaunitz, Santa Monica, Calif.

[73] Assignee: Polestar Technologies, Inc., Needham Heights, Mass.

[21] Appl. No.: 08/763,243

[22] Filed: Dec. 10, 1996

Related U.S. Application Data

[63] Continuation of application No. 08/687,761, Jul. 26, 1996, abandoned.

[51] Int. Cl.⁶ .................................................. A61B 5/097
[52] U.S. Cl. ...................... 600/529; 600/532; 250/345; 250/339.03
[58] Field of Search .................................. 600/532, 529; 356/311; 250/339.03, 345

[56] References Cited

U.S. PATENT DOCUMENTS

| | | |
|---|---|---|
| 4,830,010 | 5/1989 | Marshall .................................. 128/630 |
| 5,065,025 | 11/1991 | Doyle ....................................... 250/343 |
| 5,284,054 | 2/1994 | Loebach .................................... 73/23.3 |
| 5,317,156 | 5/1994 | Cooper et al. ........................... 250/345 |
| 5,440,664 | 8/1995 | Harrington et al. ..................... 385/125 |
| 5,486,699 | 1/1996 | Fabinski et al. ......................... 250/345 |

*Primary Examiner*—Marvin M. Lateef
*Assistant Examiner*—Eleni Mantis Mercader
*Attorney, Agent, or Firm*—Wolf, Greenfield & Sacks, P.C.

[57] ABSTRACT

Method and system for measuring the relative concentrations of first and second isotopic forms of a chemical species within a sample. The present invention need not use a laser or high resolution spectrometer. The system typically includes a waveguide cell with good transmission of particular wavelengths of IR radiation, such as a hollow glass fiber waveguide cell. A source emits electromagnetic radiation, which is modulated at first and second wavelength bands that correspond to absorption bands of the first and second isotopic forms of the chemical species, respectively. In certain embodiments, the source is a filtered broad band source, such as a plurality of LEDs. In some embodiments, an FTIR spectrometer may serve as a filtered source and signal detector.

41 Claims, 6 Drawing Sheets

SYSTEMS AND METHODS FOR MONITORING RELATIVE CONCENTRATIONS OF DIFFERENT ISOTOPIC FORMS OF A CHEMICAL SPECIES

This application is a continuation of prior application Ser. No. 08/687,761 filed Jul. 26, 1996 by Ronald H. Micheels entitled "SYSTEMS AND METHODS FOR MONITORING RELATIVE CONCENTRATIONS OF DIFFERENT ISOTOPIC FORMS OF A CHEMICAL SPECIES", now abandoned.

BACKGROUND OF THE INVENTION

1. Field of the Invention

The present invention relates generally to systems and methods designed to monitor the relative concentrations of different isotopic forms of a chemical species in a sample, and more specifically to systems and methods designed to monitor the relative concentration of $^{13}CO_2$ and $^{12}CO_2$ in human breath.

2. Discussion of the Related Art

Helicobacter pylori (H.pylori) is an organism that colonizes the mucous gel layer of the gastric antrum. This bacterium is believed to be responsible for more than twenty million cases of chronic gastritis in the United States, implicating H. Pylori as the major cause of non-autoimmune chronic gastritis. In addition, scientific data indicate that this organism may be the predominant cause of more than five million cases of peptic ulcer disease in the United States. Furthermore, prospective epidemiologic studies indicate that H. pylori may play a role in the pathogenesis of gastric cancer and lymphoma. In particular, the presence of this organism in children is suspected of producing a significant risk for the development of cancer in adulthood. Moreover, since H. Pylori is estimated to be present in about one billion people worldwide, it may be the most common human pathogen. Although at present eradication of H. Pylori is only recommended for patients with H.pylori infection and peptic ulcer disease, more wide-scale eradication programs aimed at decreasing the incidence of gastric malignancies are under consideration.

As is generally true of any test method, it is desirable to monitor the presence of H. Pylori using a minimally invasive technique. Based on its lack of invasiveness, the $^{13}C$-urea breath test is commonly believed to be the best approach to monitoring the presence of H.pylori in humans. In this test, breath samples are obtained from a patient before and after ingestion of a meal containing $^{13}C$-urea. The carbon dioxide present in a breath sample is then analyzed to determine the ratio of $^{13}CO_2$ to $^{12}CO_2$. Typically, the isotope ratio measurement is made from about 20 minutes to about 60 minutes after ingestion of the $^{13}C$-urea.

When performing a $^{13}C$-urea breath test, the criteria for a positive test response for H. pylori is a $^{13}CO_2$ to $^{12}CO_2$ ratio increase of 5 to 6 parts per thousand above the baseline ratio measured prior to ingestion of the $^{13}C$-urea. The normal baseline isotopic abundance of $^{13}C$ is about 1% while $^{12}C$ is about 99%. The combination of the low initial concentration of $^{13}CO_2$ and the small change in its concentration for the minimum positive response to the $^{13}C$-urea test requires a measurement technique with very high sensitivity to both $^{13}CO_2$ and $^{12}CO_2$, and their ratio.

Due to their high sensitivity and good signal to noise ratio, magnetic sector ratio mass spectrometers are normally employed in $^{13}C$-urea breath tests. According to this technique, the relative isotope concentrations of carbon dioxide are calculated by monitoring the size of the spectral peaks at mass numbers 44 ($^{12}CO_2$) and 45 ($^{13}CO_2$). However, the current technique has several substantial drawbacks. The mass spectrometers are relatively expensive and so are only available in a small number of specialized analytical laboratories. In addition, portions of the vacuum systems in these spectrometers require bake-out cycles on a daily basis to remove contamination, and the filaments in the ionization source typically require weekly replacement. Hence, the current apparatus has a relatively low duty cycle. Moreover, the current method also has problems with interference from $^{17}O$, which must be separately monitored, adding to the complexity of the measurement. Furthermore, the current technique requires a sample transfer step from the sample container to a vacuum system, increasing the possibility of sample contamination. Because of these factors, highly-skilled technicians are commonly used for sample preparation as well as operation and maintenance of the instrumentation. As a result, magnetic sector mass spectrometry is a relatively expensive and inconvenient analytical method for conducting $^{13}C$-urea breath tests.

Infrared (IR) absorption has also been used to measure $^{13}CO_2/^{12}CO_2$ ratios in breath samples. In IR absorption techniques, a chemical species undergoes a transition between vibrational energy states by absorbing electromagnetic radiation at a wavelength that corresponds to the energy difference between two vibrational energy levels of the chemical species. Since the difference in vibrational energy levels for a given chemical species (e.g., carbon dioxide) depends upon the mass of the chemical species, absorption of IR radiation by different isotopic forms of the chemical species (e.g., $^{13}CO_2$ and $^{12}CO_2$) can be distinguished by their respective IR absorption bands which appear at different wavelengths.

A method of performing $^{13}C$-urea breath tests by high resolution infrared absorption spectroscopy with a continuously tunable semiconductor diode laser as the source of electromagnetic radiation is disclosed in Applied Optics 32, 6727 (1993). However, as is generally true for any laser-based analytical technique, this method involves relatively expensive instrumentation and careful temperature control to avoid problems associated with laser output power and wavelength instability. Moreover, due to the relatively weak absorption of carbon dioxide at a wavelength of about 1.6 microns, this system employs a comparatively long absorption pathlength (23.6 meters), accomplished with a multiple pass cell. Furthermore, the cells have a relatively large volume of from about 300 cm³ to about 400 cm³, so more than one breath may be required to fill and flush the cells with a breath sample, reducing the practicality of this technique for breath analysis. In addition misalignment of cell mirrors due to mechanical vibrations can lead to substantial errors in the isotope ratio measurement, increasing the likelihood of unreliable results.

U.S. Pat. No. 5,394,236 and Science 263, 945 (1994) each disclose methods of conducting $^{13}C$-urea breath tests with a discretely tunable $CO_2$ gas laser. However, these techniques have the inherent stability problems of any laser-based technique as discussed above. In addition, the wavelength of the electromagnetic radiation output by the lasers is used at two different emission lines. Therefore, the systems utilize either two separate lasers or a sophisticated switching mechanism, either of which lead to increased system cost. Moreover, to avoid the relatively weak signals and long path lengths associated with transitions from the ground vibrational state of dilute concentrations of carbon dioxide, the disclosed systems in these references analyze plasma conductivity with optogalvanic effect spectroscopy. According to these methods, the breath sample is disposed within a plasma discharge to place carbon dioxide in excited vibrational energy states. A change in the conductivity of the plasma discharge due to transitions from the excited vibrational energy states is used to determine the relative concentrations of $^{13}CO_2$ and $^{12}CO_2$. While optogalvanic effect spectroscopy may avoid certain disadvantages of other analytical methods, the use of a plasma discharge results in a system having increased complexity and cost.

The Lancet 345, 961 (1995), U.S. Pat. No. 5,486,699 and Anal. Chem. 58, 2172 (1986) each disclose methods of using IR absorption to monitor the relative concentrations of $^{13}CO_2$ and $^{12}CO_2$ in a gas sample with non-dispersive IR sources. The first reference does not disclose the specific details of this technique, but the second and third references do disclose that a comparatively large sample volume (at least 500 mL) is needed. Therefore, more than one breath may be required to fill and flush the cells, reducing the practicality of this technique for breath analysis. The last reference discloses a method that involves modulating the pressure or density of a gas sample contained in four different sample cells in order to obtain good sensitivity. As a result, this technique is relatively complex and expensive to utilize.

Gastroenterology 108 (4 Suppl.), A103 (1995) discloses a system for measuring H. Pylori in humans with an IR spectrometer. The figure demonstrates fine resolution of the rotational energy transitions, indicating that a high spectral resolution was used; these high resolution spectrometers are relatively large and inconvenient and comparatively expensive to purchase. Furthermore, such spectrometers often involve relatively long data acquisition times when operated with high spectral resolution.

Gastroenterology 108 (4 Suppl.), A235 (1995) discloses the results of measurements of measuring H. Pylori in humans using an IR spectrometer. This reference does not disclose the experimental details of the method used, nor the specific apparatus used.

In addition to the $^{13}C$-urea breath test, a related $^{14}C$-urea breath test is available which takes advantage of the radioactive decay of $^{14}C$ to monitor the presence of H. Pylori in humans. The detection instrumentation for this test is based on counting radioactive decay particles and, therefore, is relatively simple and inexpensive. However, the use of a radioactive material involves substantial costs associated with safe material handling and disposal protocol. Moreover, the use of a radioactive element precludes this test from being used in children and pregnant women. This limitation is a major disadvantage since a primary target for proposed H.pylori eradication and testing programs is children.

Therefore, there is a need for a safe, simple, effective, low-maintenance and inexpensive system and method for monitoring the relative concentrations of isotopic and non-isotopic forms of a chemical species.

SUMMARY OF THE INVENTION

In one illustrative embodiment, the present invention provides a system for monitoring relative concentrations of a chemical species including first and second isotopic forms. The system comprises a sample, a source of electromagnetic radiation, a device for modulating electromagnetic radiation emitted by the source, a waveguide sample cell and a detector. The source is capable of simultaneously emitting electromagnetic radiation at first and second wavelength bands which correspond to absorption bands of the first and second isotopic forms, respectively. The waveguide sample cell contains the sample and is capable of transmitting greater than about 4% of the first and second wavelength bands of electromagnetic radiation. The system is arranged such that electromagnetic radiation emitted by the source is modulated by the device, impinges upon the sample contained within the waveguide, passes through the waveguide and impinges upon the detector.

In another illustrative embodiment, the system The system further includes first and second filters for filtering the broad band of radiation emitted by the source to define the first and second wavelength bands. In addition, the source is capable of simultaneously emitting a broad band of electromagnetic radiation that includes the first and second wavelength bands.

In a further illustrative embodiment, the present invention provides a method of measuring relative concentrations of a chemical species including first and second isotope forms. The method comprises the steps of: simultaneously emitting electromagnetic radiation at first and second wavelength bands; modulating the first and second wavelength bands of electromagnetic radiation; impinging the modulated first and second wavelengths of electromagnetic radiation upon the sample, the first wavelength band corresponding to an absorption band of the first isotopic form, the second wavelength band corresponding to an absorption band of the second isotopic form, the sample being contained within a waveguide capable of passing at least 4% of the first and second wavelength bands of electromagnetic radiation; and measuring absorption of the modulated electromagnetic radiation at the first and second wavelength bands by the first and second isotopic forms of the chemical species, respectively.

BRIEF DESCRIPTION OF THE DRAWINGS

The advantages and features of the present invention will be more clearly appreciated from the following detailed description when taken in conjunction with the accompanying drawings, in which.

DETAILED DESCRIPTION

According to the present embodiment, a system is provided that employs a waveguide sample cell to monitor the relative concentrations of $^{13}CO_2$ and $^{12}CO_2$ in a sample of human breath by IR absorption. In particular, this system may be used to perform a $^{13}C$-urea breath test for the presence of *H. pylori* in humans.

Figure 1:
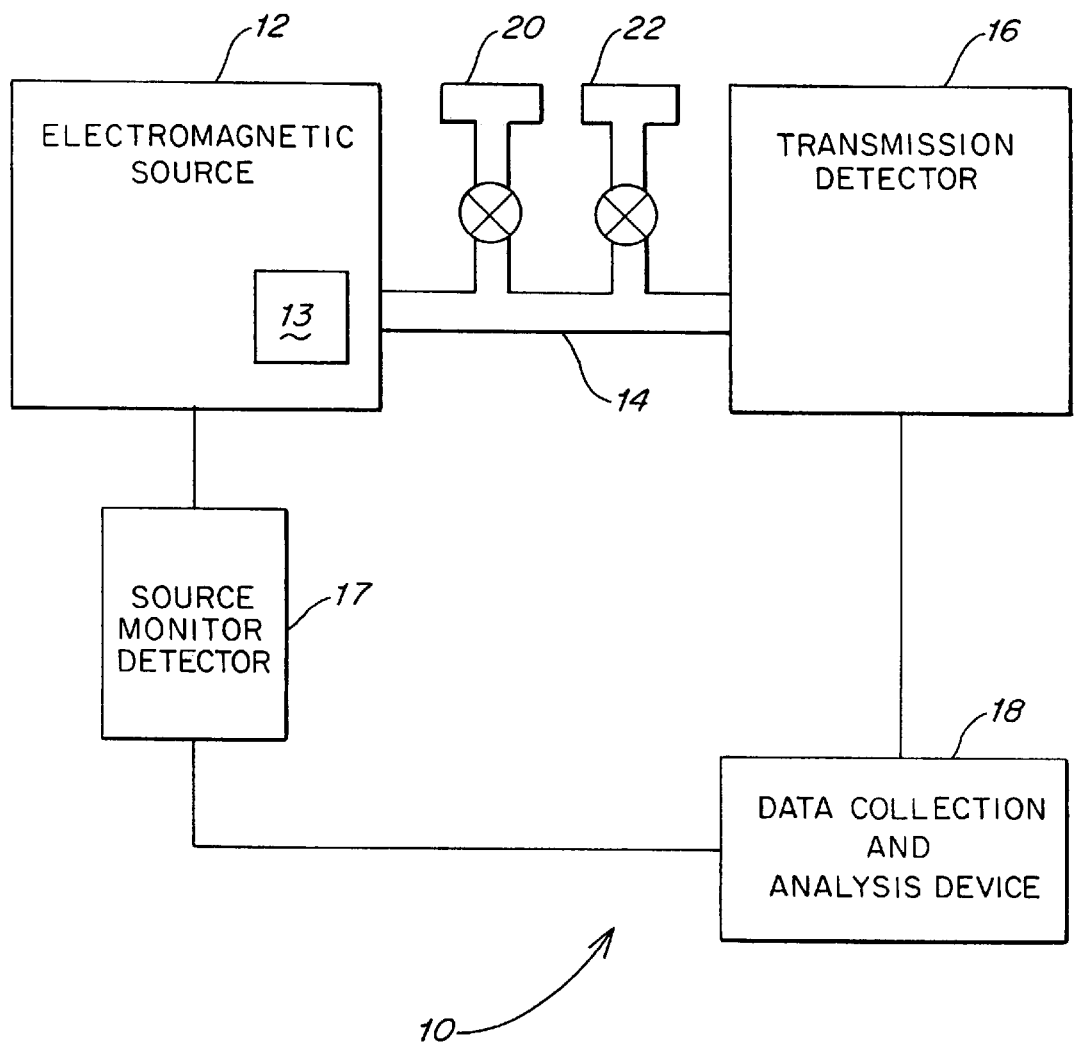
FIG. 1 is a schematic representation of one embodiment of a system according to the present invention.

FIG. 1 depicts a system 10 which includes electromagnetic radiation source 12, waveguide sample cell 14, transmission detector 16, source monitor detector 17, data collection and analysis device 18, gas inlet 20 and gas outlet 22. System 10 is arranged such that electromagnetic radiation emitted by source 12 impinges upon a breath sample contained within waveguide sample cell 14. An electronic circuit 13 within source 12 modulates the electromagnetic radiation emitted by source 12. Alternatively, the modulation device may be a mechanical device (e.g., chopper) located between source 12 and waveguide cell 14. Such circuits and devices are known to those skilled in the art and are intended to be within the scope of the present invention. The purpose of the modulation device is to turn on/off, partially attenuate or otherwise impose a pattern (change in amplitude) on the source to compensate for (filter or subtract) extraneous sources of radiation in the wavelength bands used to detect $^{13}CO_2$ and $^{12}CO_2$.

A portion of the electromagnetic radiation emitted by source 12 impinges on source monitor detector 17 before reaching the waveguide cell 14. In addition, a portion of the electromagnetic radiation between wavelengths of from about 2,000 $cm^{-1}$ to about 4,000 $cm^{-1}$ that is emitted by source 12 is absorbed by the $^{13}CO_2$ and $^{12}CO_2$ contained with the breath sample. The remainder of the electromagnetic radiation passes through waveguide 14 and is directed onto transmission detector 16. Transmission detector 16, source monitor detector 17, and/or source 12 are connected to data collection and analysis device 18 such that the amount of the electromagnetic radiation emitted by source 12 that is absorbed the by the $^{13}CO_2$ and $^{12}CO_2$ contained within the breath sample can be monitored at appropriate wavelength regions. In addition, the use of detector 17, which is in communication with device 18, allows for correction in variations of the intensity of radiation emitted by source 12 and allows for measurement of the optical throughput efficiency of system 10. Gas inlet 20 and gas outlet 22 allow the breath sample to enter and exit waveguide 14, respectively.

Figure 2:
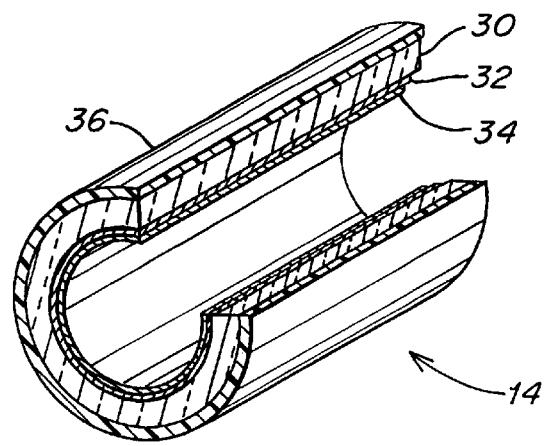
FIG. 2 is a perspective view of one embodiment of a hollow glass fiber waveguide as used in the present invention.

In a preferred embodiment, waveguide cell 14 is constructed from a hollow glass fiber waveguide adapted to hold the breath sample while conducting a $^{13}CO_2$-urea breath test for the presence of *H. Pylori*. Certain general characteristics of such hollow glass fiber waveguides useful in the present invention are disclosed in U.S. Pat. No. 5,440,664 and *Optics Letters* 19, 1034 (1994). FIG. 2 is a perspective view of one such hollow glass fiber waveguide 14 which includes tubing 30, including a double layer inner coating, including a first layer 32 and a second layer 34. Waveguide 14 further includes an outer coating 36. First layer 32 and second layer 34 each provide enhanced reflectivity of electromagnetic radiation from wavelengths of about 1,500 $cm^{-1}$ to about 4,000 $cm^{-1}$. Second layer 34 is also capable of increasing the useful lifetime of the waveguide by providing protection against corrosion of the first layer 32. In addition, outer coating 36 is designed to increase the mechanical strength of the waveguide.

In certain embodiments, tubing 30 (i.e., the substrate material) is formed from silica, nickel or certain polymeric materials. In such embodiments, first layer 32 is formed from silver, and second layer 34 is formed from silver iodide or zinc sulfide. In other embodiments, tubing 30 is formed from silver and second layer 34 is formed from silver bromide or silver iodide. For these embodiments, hollow glass fiber waveguide 14 need not include first layer 32. In all of these embodiments, outer coating 36 is formed from a polymeric material, such as a polyimide or a UV-acrylic. In those embodiments in which tubing 30 is formed from a polymeric material, the waveguide 14 need not include outer coating 36. While certain combinations of materials appropriate for use in hollow glass fiber waveguide 14 have been disclosed herein, other combinations of materials that offer similar performance characteristics are known to those skilled in the art and are contemplated to be within the scope of the present invention.

In this embodiment, the particular combination of materials used in the construction of waveguide 14 is selected to maximize the transmission of electromagnetic radiation having a wavelength of from about 2,000 $cm^{-1}$ to about 4,000 $cm^{-1}$ through waveguide 14. Conventional waveguides, such as single layer gold coated light pipes, transmit only a nominal amount (4% or less) of incident radiation between wavelengths of from about 2,000 $cm^{-1}$ to about 4,000 $cm^{-1}$ for a one meter pathlength. In contrast, a double layer coated hollow glass waveguide of 1 meter pathlength is capable of transmitting about 72% of the incident radiation in the same wavelength range. Accordingly, waveguide 14 should transmit a significant amount (i.e., at least about 10%) of incident radiation between wavelengths of from about 2,000 $cm^{-1}$ to about 3,000 $cm^{-1}$ for a one meter pathlength. For a one meter pathlength, waveguide 14 preferably transmits at least about 30% of electromagnetic radiation having a wavelength of from about 2,000 $cm^{-1}$ to about 3,000 $cm^{-1}$, more preferably at least about 50% and most preferably at least about 70%.

The thicknesses of the various layers of waveguide 14 are selected to provide corrosion resistance and mechanical strength as well as the transmission properties noted above. In addition, in certain embodiments waveguide 14 may be configured as a bent or coiled structure to reduce the overall size of system 10. It should be noted that the double layer reflective coating also minimizes transmission losses associated with waveguide bending. Thicknesses appropriate for use for the various layers of hollow glass fiber waveguide 14 are known to those skilled in the art.

When performing a $^{13}C$-urea breath test for the presence of *H. pylori*, the amount of $^{12}CO_2$ in the breath sample is usually about one hundred times greater than the amount of $^{13}CO_2$ present in the same sample. Therefore, to increase the sensitivity of the measurement of the relative concentrations of $^{13}CO_2$ and $^{12}CO_2$ in the breath sample, it is desirable that the hollow glass fiber waveguide cell 14 have a relatively long pathlength. By "pathlength" it is herein meant to refer to the distance that a photon of electromagnetic radiation emitted by source 12 travels through a sample disposed within waveguide cell 14 prior to being detected by detector 16. Preferably, waveguide cell 14 has a pathlength of from about 30 cm to about 100 cm and more preferably from about 50 cm to about 100 cm.

The sensitivity of an IR absorption experiment can depend upon the pathlength, absorption coefficient and the sample concentration. If the pathlength is too long or the carbon dioxide concentration is too high, one or more absorption features may become saturated, causing reduced sensitivity for these features. Alternatively, if the pathlength is too short or the carbon dioxide concentration is too low, one or more absorption features may not be strong enough to distinguish from the baseline noise, resulting in unacceptably low sensitivity for these features. Therefore, system 10 should be arranged such that the pathlength of waveguide 14 and the concentration of carbon dioxide contained within waveguide 14 result in optimal absorption of IR radiation by both $^{13}CO_2$ and $^{12}CO_2$ in the sample. Preferably, the pathlength of waveguide cell 14 and characteristic absorption bands of carbon dioxide for $^{13}$C-urea breath test samples are selected such that the absorbance of a baseline sample of human breath at the characteristic carbon dioxide absorption bands (i.e., a sample having the natural abundance of $^{13}CO_2$ and $^{12}CO_2$) is greater than about 0.1, more preferably from about 0.2 to about 0.8 and most preferably from about 0.5 to about 0.6. To achieve these absorbance values with a waveguide cell having a pathlength of about 50 cm to about 100 cm, it is desirable to use the $v_3$ absorption band for $^{13}CO_2$ and the weaker $(v_1+v_2)$ and/or $(v_2$ or $v_3)$ combination absorption bands for the $^{12}CO_2$ measurement.

To optimize the efficiency and convenience associated with $^{13}$C-urea breath testing for the presence of *H. pylori*, it is advantageous to use a system in which the sample is housed in waveguide cell 14 having a volume that is less than the volume of a typical human breath to provide for complete flushing of the cell volume with the breath sample. In a preferred embodiment, the volume of waveguide cell 14 is less than about one tenth the volume of a typical human breath. However, as discussed above, it is advantageous for waveguide cell 14 to have a relatively long pathlength. Therefore, since the volume of waveguide 14 from which the cell is constructed is a function of its length and its diameter, a cylindrical waveguide cell 14 should have a comparatively small inside diameter. Preferably, waveguide cell 14 has a diameter of from about 0.3 mm to about 2 mm, more preferably from about 1 mm to about 2 mm and most preferably from about 1.3 mm to about 2 mm.

Figure 3:
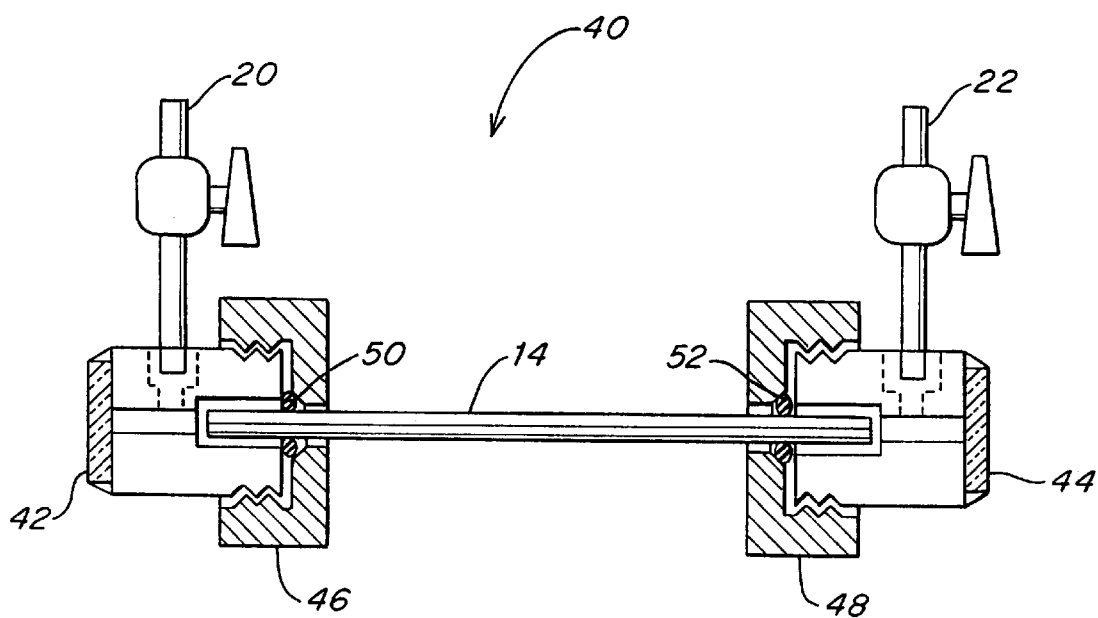
FIG. 3 is a schematic representation of one embodiment of a waveguide based absorption cell according to the present invention.

FIG. 3 shows in more detail one arrangement of a waveguide based absorption cell 40, which is one portion of system 10. Cell 40 is arranged to optimize the transmission of electromagnetic radiation having wavelengths of from about 2,000 cm$^{-1}$ to about 4,000 cm$^{-1}$ through the gas sample contained in waveguide 14. In addition to waveguide 14, cell 40 includes gas inlet 20 and gas outlet 22, and IR transparent windows 42 and 44, respectively. Cell 40 further includes modified compression fittings 46 and 48 as well as O-ring seals 50 and 52. Fittings 46 and 48 and seals 50 and 52 are designed to physically connect waveguide 14 to gas inlet 20, gas outlet 22 and windows 42 and 44 such that cell 40 can be readily incorporated into system 10 while allowing a sample to easily enter or exit waveguide 14.

Gas inlet 20 and gas outlet 22 should prevent escape of the breath sample over the same time period. Such gas inlets and outlets are known to those skilled in the art to include, for example, one-way valves and manually controlled shut-off valves.

IR transparent windows 42 and 44 should be formed from a material that exhibits high transmission of electromagnetic radiation having a wavelength of from about 2,000 cm$^{-1}$ to about 4,000 cm$^{-1}$. Preferably, windows 42 and 44 are formed from ZnSe, BaF$_2$, sapphire or fluorinated polyolefins, such as Teflon®. In one embodiment, windows 42 and 44 are formed from Teflon® and are press fit or molded onto waveguide 14. Other shapes and types, as well as methods of incorporating them into absorption cell 40, are known to those are known to those skilled in the art.

Figure 4:
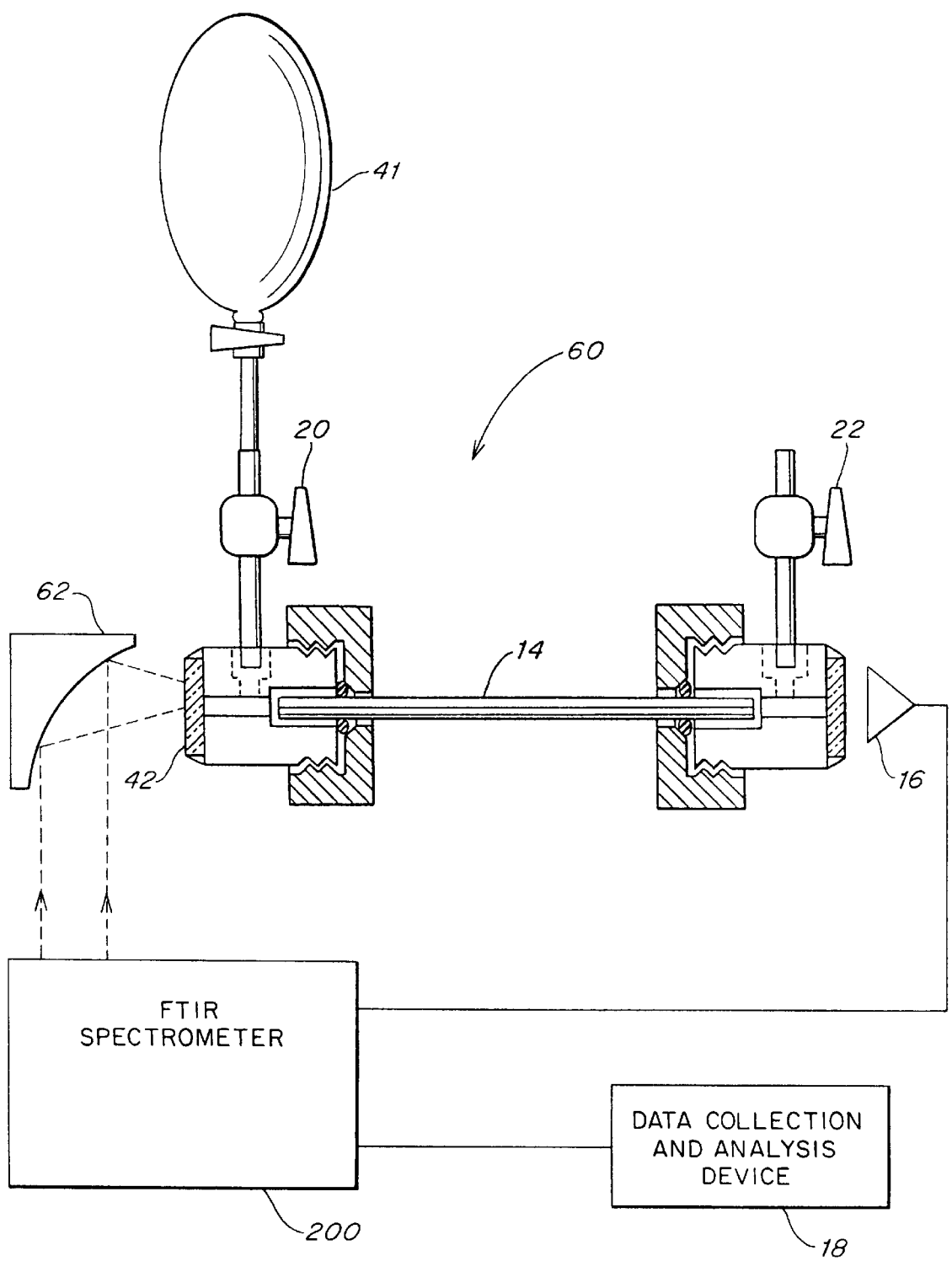
FIG. 4 is a schematic representation of one embodiment of a system according to the present invention in which an FTIR spectrometer is used as the source of electromagnetic radiation and a detection system.

FIG. 4 depicts an embodiment of a system 60 in which source 12 and source monitor detector 17 and transmission detector 16 are all provided by a Fourier transform infrared (FTIR) spectrometer 200. An air bag 41 with a disposable mouthpiece and drying filter (not shown) is in fluid communication with gas inlet 20 such that a sample of human breath stored in bag 41 can be transferred to inlet 20. System 60 further includes a beam condensing mirror 62 which reflects electromagnetic radiation emitted by FTIR spectrometer 200 and forms a condensed beam of the electromagnetic radiation which enters waveguide 14 through IR transparent window 42. While FIG. 4 depicts system 60 including air bag 41, it is to be understood other embodiments of the present invention may or may not include such an air bag.

Utilization of an FTIR spectrometer as a source and detection system is advantageous because FTIR spectrometers are readily available as well as relatively inexpensive to purchase, maintain and operate. FTIR spectrometers appropriate for use in the present invention are limited only in that they should be capable of being optically coupled to waveguide 14. It is to be noted that many FTIR spectrometers are used with gas sample cells having relatively large volumes (i.e., considerably larger than the typical volume of a human breath). Such FTIR spectrometers may be used in the present invention so long as they are capable of being modified such that waveguide cell 14 may be used as the sample cell. Methods of making these modifications to FTIR spectrometers are known to those skilled in the art.

Condensing mirror 62 may be formed from any material having a high reflectivity of electromagnetic radiation between wavelengths of from about 2,000 cm$^{-1}$ to about 3,000 cm$^{-1}$. Materials appropriate for use as mirror 62 include copper, gold and aluminum. Preferably, mirror 62 includes a substantially parabolic surface which reflects the radiation emitted by FTIR spectrometer 200 into waveguide 14. In one embodiment, mirror 62 has a focal length of from about 2 cm to about 20 cm. Typically, this surface is formed from aluminum or gold. Mirrors appropriate for use are known to those skilled in the art and are available from, for example, Space Optics Research Labs, located in Chelmsford, Mass.

Figure 5:
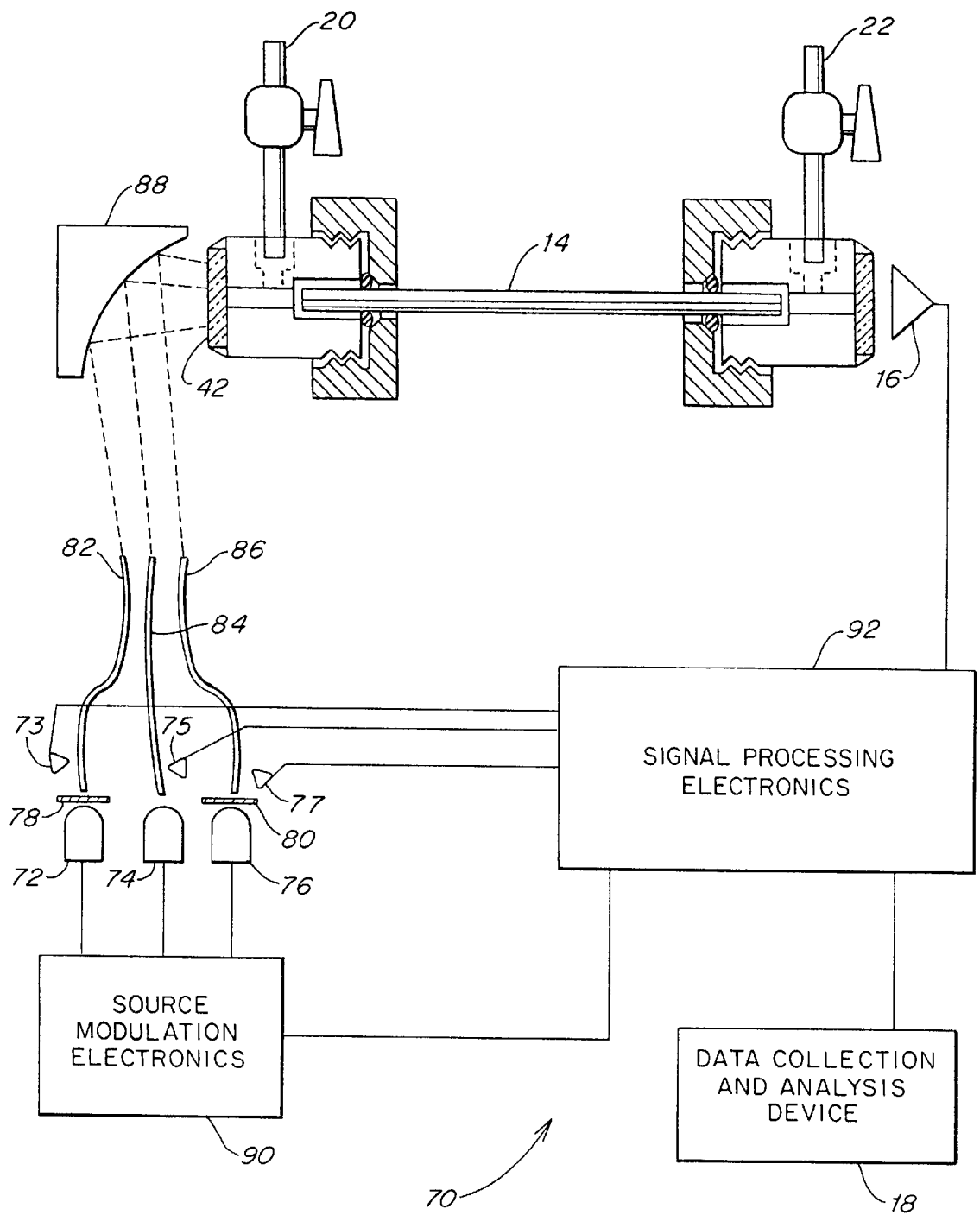
FIG. 5 is a schematic representation of one embodiment of a system according to the present invention in which three LEDs are used as the source of electromagnetic radiation.

FIG. 5 depicts an embodiment of a system 70 in which source 12 is formed from three different light emitting diodes (LEDs) 72, 74 and 76, each of which has a source monitor detector 73, 75 and 77, respectively. System 70 further includes IR bandpass interference filters 78 and 80 as well as IR transmitting optical fibers 82, 84 and 86. In addition, system 70 includes waveguide input coupling mirror 88, source modulation electronics 90 and signal processing electronics 92. Waveguide 14, gas inlet 20 and gas outlet 22 are arranged as shown in FIG. 3.

LED 72 emits electromagnetic radiation having wavelengths of from about 2225 cm$^{-1}$ to about 2290 cm$^{-1}$. This wavelength range is used to detect $^{13}CO_2$ by absorption of electromagnetic radiation at wavelengths of from about 2225 cm$^{-1}$ to about 2282 cm$^{-1}$, corresponding to the $v_3$ mode of $^{13}CO_2$. Such LEDs are known to those skilled in the art and may be purchased from, for example, Rainbow Optics, Co, located in Salem, Mass.

LED 74 emits electromagnetic radiation having wavelengths of from about 2900 cm$^{-1}$ to about 3000 cm$^{-1}$ which is used to provide a baseline signal level to adjust for any fluctuations in the intensity of electromagnetic radiation emitted by LED sources 72 and 76, transmitted by waveguide 14 or detected by detector 16 that arise from changes in the transmission of waveguide 14 or from changes in the detection efficiency of detector 16. Such changes may be caused by various sources, such as, for example, bending waveguide 14 or corrosion of waveguide 14 or changes in the detector temperature. LEDs appropriate for use as LED 74 are known to those skilled in the art and are available from several suppliers, including, for example, Rainbow Optics, Co.

Figure 6:
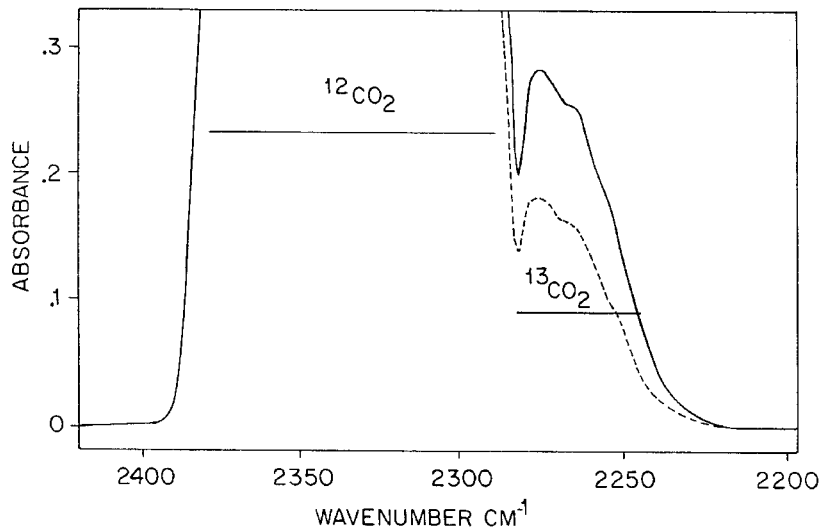
FIG. 6 depicts FTIR spectra of two human breath samples prepared according to one method of the present invention which have significantly different $^{13}CO_2$ to $^{12}CO_2$ isoptic compositions.
Figure 7:
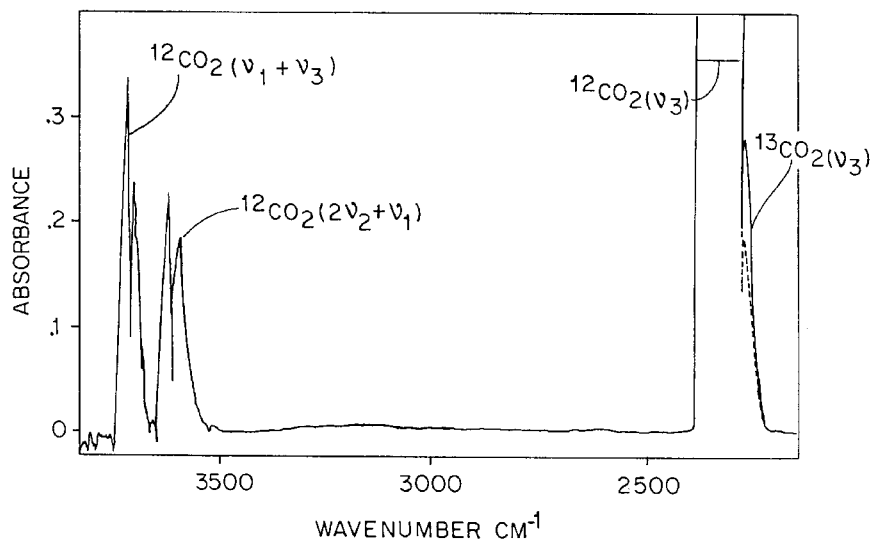
FIG. 7 shows one portion of the FTIR spectra of FIG. 6.

LED 76 emits electromagnetic radiation having wavelengths of from about 3500 cm$^{-1}$ to about 3750 cm$^{-1}$ and is used to detect the $(v_1+v_3)$ and the $(v_2+v_3)$ mode of $^{12}CO_2$. It can be advantageous to detect these modes of $^{12}CO_2$ since the $v_3$ mode of $^{12}CO_2$, appearing at about 2350 cm$^{-1}$, may become saturated at carbon dioxide levels present in breath samples. Furthermore, measuring the $(v_1+v_3)$ or $(v_2+v_3)$ modes of $^{12}CO_2$ and the $v_3$ mode of $^{13}CO_2$ during a $^{13}C$-urea breath test is desirable because these modes have about the same intensity for typical breath samples (FIGS. 6 and 7). LEDs emitting in the 3,500–3,700 cm$^{-1}$ range are known to those skilled in the art and may be purchased from, for example, Rainbow Optics, Co.

Under certain conditions of operation, the intensity of electromagnetic radiation emitted by each of LEDs 72, 74 and 76 may independently fluctuate as a function of time due to factors such as, for example, variation in room temperature. However, since each of LEDs 72, 74 and 76 is used to supply information about different components of the sample contained in waveguide cell 14, it is desirable to correct for these fluctuations to avoid making erroneous measurements on the relative concentrations of $^{13}CO_2$ and $^{12}CO_2$ contained within the sample. Detectors 73, 75 and 77, which may be photodiode detectors, are arranged to correct for these fluctuations by measuring the intensity of electromagnetic radiation emitted by LEDs 72, 74 and 76, respectively, prior to transmission into hollow waveguide cell 14. The intensity of electromagnetic radiation measured by detector 16 at the corresponding wavelength ranges for LEDs 72, 74 and 76 is then normalized by the signal measured from detectors 73, 75 and 76, respectively. As known to those skilled in the art, detectors appropriate for use as detectors 73, 75 and 76 in the 2,000–4,000 cm$^{-1}$ range, are commercially available.

IR bandpass interference filters 78 and 80 are designed to narrow the range of wavelengths of electromagnetic radiation emitted by LEDs 72 and 76, respectively, which reach hollow glass fiber waveguide cell 14. Filter 78 may be any filter capable of passing wavelengths of from about 2225 cm$^{-1}$ to about 2290 cm$^{-1}$ while blocking substantially all the electromagnetic radiation outside this range. Filter 80 may be any filter capable of passing wavelengths of from about 3500 cm$^{-1}$ to about 3750 cm$^{-1}$ while blocking substantially all the electromagnetic radiation outside this range. Commercially available IR bandpass interference filters appropriate for use as filters 78 and 80 are known to those skilled in the art and may be purchased from, for example, (Spectrogen U.S., Parsipanny, N.J.).

Optical fibers 82, 84 and 86 are used to relay the electromagnetic radiation from LEDs 72, 74 and 76 to the focal region of waveguide input coupling mirror 88 and to increase the quality of the optical coupling of LEDs 72, 74 and 76 with waveguide cell 14. In this regard, fibers 82, 84 and 86 assist by causing the electromagnetic radiation to reflect off mirror 88 and focus into a relatively narrow beam that enters waveguide 14 through IR transparent window 42. Accordingly, optical fibers 82, 84 and 86 should be capable of transmitting a relatively high percentage of incident electromagnetic radiation between wavelengths of from about 2000 cm$^{-1}$ to about 4000 cm$^{-1}$. Materials appropriate for use as fibers 82, 84 and 86 are known to those skilled in the art and include, for example, ZnSe. In one embodiment, optical fibers 82, 84 and 86 are formed from GeAsSeTe. Generally, fibers appropriate for use as optical fibers 82, 84 and 86 are known to those skilled in the art and may be purchased from, for example, SpectraTech, Inc., located in Stamford, Conn.

Waveguide input coupling mirror 88 should be capable of reflecting a comparatively high percentage of electromagnetic radiation between wavelengths of from about 2000 cm$^{-1}$ to about 4000 cm$^{-1}$. Preferably, the surface of mirror 88 which is exposed to electromagnetic radiation output by LEDs 72, 74 and 76 has a substantially parabolic shape. Typically, the surface of mirror 88 is formed from gold or aluminum. Preferably, mirror 88 has a focal length of from about 2 cm to about 20 cm. Mirrors appropriate for use as waveguide input coupling mirror 88 are known to those skilled in the art and may be purchased from, for example, Space Optics Research Lab.

In some embodiments, the chips for LEDs 72, 74 and 76 may be mounted together in a closely spaced array in a single metal can such that system 70 need not include optic fibers 82, 84 and 86 to condense the LED output into a small area. LED chips and packaging procedures appropriate for use in such embodiments of the present invention are known to those skilled in the art.

The amount of electromagnetic radiation absorbed by the sample for each of LEDs 72, 74 and 76 is selectively measured by detector 16 using source modulation electronics 90 and signal processing electronics 92 including synchronous demodulation. In one embodiment, source modulation electronics 90 pulses LEDs 72, 74 and 76 such that, at any given time during a $^{13}C$-urea breath test, only one of these LEDs emits electromagnetic radiation. In another embodiment, source modulation electronics 90 modulates LEDs 72, 74, and 76 with square wave modulation at different modulation frequencies. Signal processing electronics 92 (available in a desktop unit from EG&G-PAR, located in Princeton, N.J.; or an IC chip form from Analog Devices, located in Norwood, Mass.) utilizes lock-in detection or phase sensitive digital signal processing techniques to improve the signal/noise ratio and sensitivity of the signal measured by detector 16. The final output of the desired isotope ratio may be determined by electronically subtracting and calculating the ratio of the three LED signals according to the following equation:

$$^{13}CO_2{:}^{12}CO_2=[abs(LED\ 72)-abs(LED\ 74)]/[abs(LED\ 76)-abs(LED\ 74)]$$

where "abs(LED 7X)" is the absorbance of the sample at the wavelength bands of radiation emitted by LED 7X.

Detectors appropriate for use as detectors 16 and 17 are known to those skilled in the art. These detectors include, but are not limited to: PbSe (available from Graseby Infrared, located in Orlando, Fla.); InSb (available from EG&G/Judson, located in Montgomeryville, Pa.); InAs, HgCdTe (available from EG&G/Judson); and photovoltaic or photoconductive detectors. When using such detectors during a $^{13}C$-urea breath test, reducing the temperature of detectors 16 and 17 improves the sensitivity by reducing background noise. Therefore, the above-listed detectors are typically cooled by one to three-stage thermoelectric coolers to maintain detector 16 and 17 at a temperature of from about 200° C. to about 270° C. Such cooling systems are known to those skilled in the art. Alternatively, detectors 16 and 17 may be cooled by a closed cycle helium compressor for maintaining detectors 16 and 17 at a temperature of about 77° K. Such cooling systems are known to those skilled in the art. In one embodiment, detector s16 and 17 are a deuterated tryglyceral sulfate (DTGS) IR detector, available from GEC-Marconi, located in San Diego, Calif. In this embodiment, detectors 16 and 17 may achieve a good signal to noise ratio while operating at room temperature, so detectors 16 and 17 need not be cooled by an external source.

Data collection and analysis device 18 may be any apparatus that is capable of electronically monitoring the signal measured by detectors 16 and 17 as a function of wavelength. Typically, device 18 is a commercially available microcomputer and associated peripherals. Such devices are known to those skilled in the art.

While the present application has emphasized the use of a hollow waveguide for cell 14, it is also contemplated that cell 14 may be a different cell so long as such a cell provides good transmission of infrared electromagnetic radiation without excessive cell volume and without the use of a laser or high resolution spectrometer as source 12. For example, in one embodiment, cell 14 may be a light-pipe absorption cell. Such cells may have pathlengths of about 50 cm. Although these light-pipe absorption cells may have increased volume and reduced transmission relative to hollow waveguides, they may have the advantage of being compatible with standard FTIR sample chambers. In addition, these light-pipe absorption cells still provide the desirable level of sensitivity for use in $^{13}$C-urea breath tests.

According to the present invention, a light-pipe absorption cell should transmit at least about 20% of electromagnetic radiation between wavelengths of about 2,000 cm$^{-1}$ to about 4,000 cm$^{-1}$. In one embodiment, cell 14 is a Macro Lightpipe Gas Cell, available from Spectra-Tech Inc., located in Shelton, Conn. This gas cell has a volume of about 135 ml, a pathlength of about 50 centimeters, a length of about 75 mm and a diameter of about 46 mm. The body is constructed from precision bore glass with gold plating on the internal cell wall. This gas cell employs multiple internal reflection to achieve a relatively long pathlength to volume ratio while providing an acceptable transmission of electromagnetic radiation between wavelengths of about 2,000 cm$^{-1}$ to about 4,000 cm$^{-1}$.

In practice, the systems described herein (FIGS. 1–5) may be employed to perform clinical sampling in three different modes. In a first mode, exhaled breath is directly sampled by having a patient breath into a tube directly connected to the gas inlet 20 of the waveguide cell. In this mode of sampling, the breath sample can be measured as soon as it is collected in the cell. In a second mode, the patient breathes into a tube connected with the gas inlet of a disposable version of the cell. When the disposable cell is filled with the breath sample, valves in the gas inlet and gas outlet are closed manually or automatically, and the sample cell containing the breath sample is transported to a measurement system which is kept at a remote location relative to the sampling site. In the second sampling mode, the measurement system employs a removable sample cell which is mounted and unmounted for each measurement. In certain embodiments of the second sampling mode, the cell is reusable. In a third sampling mode, a breath sample is collected in a container, such as a plastic gas sample bag, at a site remote from the measurement system. The sample is transported to the measurement system and subsequently transferred into a permanently mounted cell in the measurement system. With the first two sampling modes, the risk of partial or complete loss of the breath sample during a container to container transfer step and the risk of improper sample identification is reduced or eliminated. In contrast, the more conventional sampling procedures used in mass spectral breath analysis have a relatively high probability of incurring such sample loss.

Although the present application has emphasized the use of systems for measuring the relative concentrations of $^{13}CO_2$ and $^{12}CO_2$ in human breath samples for investigating the presence *H. pylori*, these systems may also be used to study the relative concentrations of $^{13}CO_2$ and $^{12}CO_2$ in human breath samples used for other medical tests such as those investigating intestinal transit and gastric emptying, exocrine pancreatic function, starch digestion, and metabolic rate during exercise. Furthermore, the present invention contemplates the use of such systems for monitoring the relative concentrations of isotopic forms of a variety of chemical species, such as ammonia or water.

A "chemical species" as used herein refers to any polyatomic entity. Therefore, a chemical species may be a molecule, a cation, an anion or a free radical. Different isotopic forms of a chemical species are variations of a chemical species having different numbers of neutrons. Examples include $^{14}NH_3$ and $^{15}NH_3$, or $H_2O$ and $D_2O$.

The following example is illustrative of one embodiment of the present invention and is not intended to be construed as limiting.

EXAMPLE

Simulated breath samples were tested using a system substantially as shown in FIG. 4. A ten inch drying filter (Drierite™ drying column) and a 0.4 liter Tedlar™ gas sampling bag (both available from Fisher Scientific, located in Pittsburgh, Pa.) were used. The bag was fitted with a stainless steel valve to the gas inlet. The system also included a Perkin-Elmer FTIR spectrometer (Norwalk, Conn.) and a 40 centimeter pathlength hollow glass fiber waveguide with a Ag/AgI internal coating.

The simulated urea breath samples with a range of $^{13}CO_2/^{12}CO_2$ values were generated by human ingestion of between about 500 and about 900 milligrams of an isotopic form of aqueous sodium bicarbonate, (i.e., an aqueous solution of $NaH^{13}CO_3$) and collecting breath samples at different delay times after ingestion of the bicarbonate. According to this technique, carbon dioxide is formed by the reaction of sodium bicarbonate with hydrochloric acid present in stomach. The carbon dioxide diffuses into the blood and lungs, ultimately being exhaled. Each breath sample was passed through the drying column to remove water vapor from the sample and was then collected in the sampling bag. One half of each breath sample was transferred into the waveguide cell by squeezing the sampling bag. The waveguide cell containing the breath sample was then isolated by closing the inlet and outlet valves.

FTIR absorption spectra of a sample of naturally occurring carbon dioxide and of a breath sample prepared as described above are shown in FIGS. 6 and 7 (dashed lines correspond to $^{13}$C unenriched breath samples; solid lines correspond to breath samples taken after $NaH^{13}CO_3$ ingestion). These spectra were processed with a personal computer using the Graham's 386 Software Package (Gallactic, Inc., located in Salem, N.H.). Due to the low natural isotopic abundance of $^{13}$C, the absorption intensity of the $v_3$ mode of $^{13}CO_2$ at about 2250 cm$^{-1}$ is about 100 times weaker than the absorption intensity of the $v_3$ mode of $^{12}CO_2$ at about 2350 cm$^{-1}$.

FIG. 7 indicates that the $v_3$ mode of $^{12}CO_2$ at about 2350 cm$^{-1}$ is saturated, so this mode was not be used to determine the relative concentrations of $^{13}CO_2$ and $^{12}CO_2$ in the sample. Instead, the relative concentrations of $^{13}CO_2$ and $^{12}CO_2$ in the samples were measured by integrating the appropriate spectral band areas for bands corresponding to the $v_3$ mode of $^{13}CO_2$ and the $(v_1+v_3)$ plus the $(v_2+v_3)$ modes of $^{12}CO_2$. In addition, it is particularly convenient use the $(v_1+v_3)$ and $(v_2+v_3)$ modes of $^{12}CO_2$ since the absorbance of this mode has about the same value as the $v_3$ mode of $^{13}CO_2$ for the concentrations of $^{12}CO_2$ and $^{13}CO_2$ encountered in these experiments.

As known to those skilled in the art, the ratio of the raw peak areas for these two species was multiplied by a correction factor equal to the known, naturally occurring isotope ratio of $^{12}CO_2$ to $^{13}CO_2$ divided by the raw IR peak area ratio of a breath sample taken prior NaH$^{13}CO_3$ ingestion, to yield the ratio of $^{13}CO_2$ to $^{12}CO_2$. It is to be noted that this analysis could also be performed using a multivariate calibration method such as partial least squares analysis to generate a calibration relation between a set of spectra and a corresponding set of known analyte values. One example of such a method involves the use of the Grams/386, PLS-Plus add-on, available from Galactic Industries. When using such a method, regions of the spectrum where there is substantial overlap between the absorption peaks of the two species can be used, increasing the number of spectral data points used in the analysis.

The spectra shown in FIGS. 6 and 7 were recorded with a spectral resolution of about 4 cm$^{-1}$. Based on these spectra, it was calculated, using the separation between absorption bands, that sufficient information to accurately measure the ratio of the isotopic and non-isotopic forms of carbon dioxide could be accomplished with a spectral resolution of only 50 cm$^{-1}$ for $^{13}CO_2$ and 200 cm$^{-1}$ for $^{12}CO_2$. In addition, FIGS. 6 and 7 demonstrate that a 40 centimeter absorption cell pathlength results in a peak absorption value of about 0.23 with 4 cm$^{-1}$ resolution, for $^{13}CO_2$ at the natural abundance level. As discussed above, an absorbance of about 0.5 can be advantageous for precise measurements of this molecular species. Therefore, to obtain this absorbance at this sample concentration, the waveguide should have a pathlength of about 1 meter.

The uncertainty of the IR spectral measurements of the ratio of $^{13}CO_2$ to $^{12}CO_2$ for a sample was determined from the standard deviation of three repeat measurements of the baseline ratio of $^{13}CO_2$ to $^{12}CO_2$ taken prior to the ingestion of bicarbonate. Using this method, the standard deviation was calculated to be about 2 parts per thousand which is approximately the required sensitivity of about 1.0 to about 2.0 parts per thousand for detection of *H.pylori*.

Figure 8:
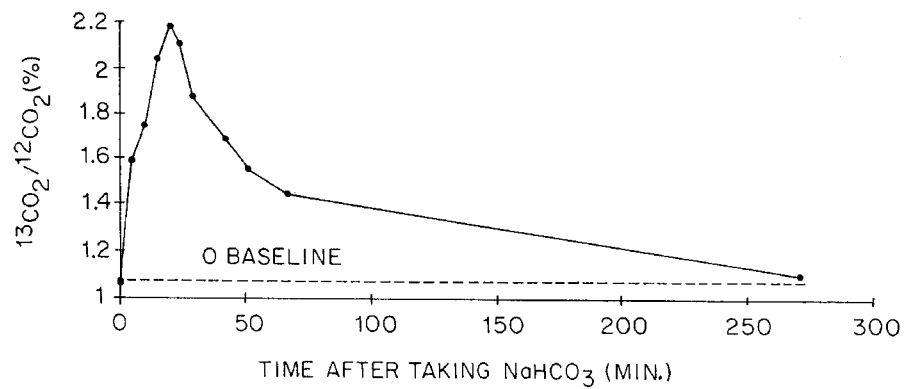
FIG. 8 is a time profile of the ratio of $^{13}CO_2$ to $^{12}CO_2$ in a sample of human breath prepared according to one method of the present invention following ingestion of a source of $^{13}CO_2$.

FIG. 8 shows a time profile of the ratio of the amount of $^{13}CO_2$ to $^{12}CO_2$ measured with the IR spectral method. FIG. 8 demonstrates that the concentration of $^{13}CO_2$ reaches a peak after about 30 minutes but remains significantly above the initial baseline value after about 4.5 hours.

Magnetic sector ratio mass spectrometry measurements of remaining portions of the samples were performed at Metabolic Solutions (Merrimack, N.H.).

Figure 9:
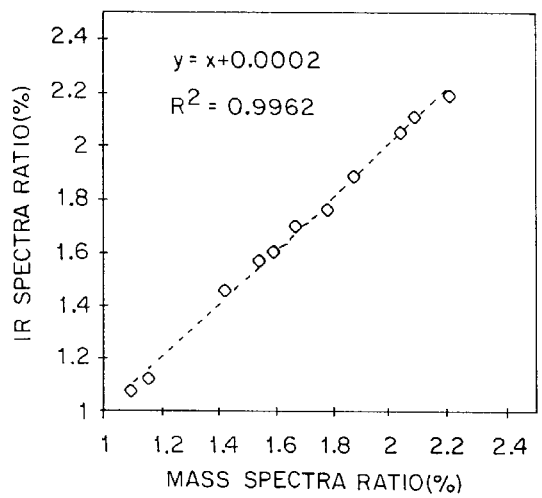
FIG. 9 is a calibration plot showing the correlation between $^{13}CO_2/^{12}CO_2$ ratios determined by a method according to the present invention and a magnetic sector mass spectrometric method.

FIG. 9 depicts a calibration plot of the $^{13}CO_2$ to $^{12}CO_2$ ratio in human breath samples (in units of percent $^{13}CO_2$) for the above-described IR absorption method relative to the magnetic sector ratio mass spectrometry method. The calibration plot includes a linear regression fit which exhibits a correlation coefficient of about 0.996. Since the correlation coefficient has a maximum possible value of 1.0, FIG. 9 demonstrates that a very close correlation exists between these two methods.

In certain embodiments, it is an advantageous feature of the present invention that the system is designed such that it may be readily dismantled and portions (e.g., the waveguide cell) of the system can be thrown away. For these embodiments, plastic fittings may be used for the sample inlet and outlet. Plastic tubing may also be included within such systems such that the sample inlet and outlet are in fluid communication with the waveguide cell. In certain embodiments systems in accordance with the present invention may be designed for single use applications.

Having thus described certain embodiments of the present invention, various improvements, modifications and alterations will be obvious to those skilled in the art and are intended to be within the scope of the present invention. For example, any of a variety of lasers may be used as a source of electromagnetic radiation in the present invention. Alternatively, many different broad band radiation sources, such as a globar source, may be used in conjunction with IR filters. Accordingly, the foregoing description is by way of example only and it is not intended as limiting.

We claim:

1. A system for monitoring relative concentrations of a chemical species, the system comprising:

a sample including first and second isotopic forms of the chemical species;

a source for simultaneously emitting electromagnetic radiation at first and second wavelength bands, the first wavelength band corresponding to an absorption band of the first isotopic form, the second wavelength band corresponding to an absorption band of the second isotopic form;

a device for modulating the electromagnetic radiation emitted by the source at the first and second wavelength bands;

a waveguide cell defining a sample cell having a pathlength of from about 30 centimeters to about 100 centimeters and an inner diameter of from about 0.3 millimeters to about 2.0 millimeters; and a detector for detecting the first and second wavelength bands, wherein the system is arranged such that at least a portion of the electromagnetic radiation emitted by the source is modulated by the device, enters the waveguide, impinges upon the sample contained within the sample cell defined by said waveguide cell, and at least 10% of the first and second wavelength bands of the portion of the electromagnetic radiation that enters the waveguide cell passes through the waveguide cell and impinges upon the detector.

2. The system according to claim 1, wherein the waveguide cell is a hollow waveguide cell.

3. The system according to claim 2, wherein the hollow waveguide cell includes a substrate material formed from metal or plastic.

4. The system according to claim 2, wherein the hollow waveguide cell includes a substrate material formed from silica.

5. The system according to claim 1 wherein the system is arranged such that at least about 30% of the first and second wavelength bands of electromagnetic radiation that enters the waveguide cell is transmitted through the waveguide cell to the detector.

6. The system according to claim 1, wherein the source is a broad band source, and wherein the system further comprises filters to define the first and second wavelength bands.

7. The system according to claim 1, wherein the source and detector include a Fourier transform infrared spectrometer.

8. The system according to claim 1, wherein the source is formed from first and second light emitting diodes, the first light emitting diode emitting electromagnetic radiation at the first wavelength band, and the second light emitting diode emitting electromagnetic radiation at the second wavelength band.

9. The system according to claim 8, wherein the source further includes a third light emitting diode, the third light emitting diode emitting electromagnetic radiation at a third wavelength band located between the first and second wavelength bands, and wherein the system further comprises a source monitor detector disposed between the source and the waveguide cell, and wherein a portion of the electromagnetic radiation at the first, second and third wavelength bands emitted by the source impinge upon the source monitor detector to correct for variations in an intensity of the electromagnetic radiation emitted by the source at the first, second and third wavelength bands.

10. The system according to claim 1, wherein the sample is a sample of human breath, the first isotopic form is $^{12}CO_2$ and the second isotopic form is $^{13}CO_2$.

11. The system according to claim 1, wherein the source emits a third wavelength band of electromagnetic radiation, the third wavelength band being between the first and second wavelength bands, and not absorbed by said sample such that transmission of the third wavelength band changes with variations in an optical throughput efficiency of the system, wherein the third wavelength band is emitted by the source, modulated by the device, impinges on the waveguide sample cell and the sample and is detected by the detector.

12. The system according to claim 11, further comprising a source monitor detector disposed between the source and the waveguide cell,
wherein a portion of the electromagnetic radiation at the first, second and third wavelength bands emitted by the source impinge upon the source monitor detector to correct for variations in an intensity of the electromagnetic radiation emitted by the source at the first, second and third wavelength bands.

13. The system according to claim 11, wherein the source emits a fourth wavelength band, a distance between the third wavelength band and the first wavelength band being less than a distance between the fourth wavelength band and the first wavelength band, a distance between the fourth wavelength band and the second wavelength band being less than a distance the third wavelength band and the second wavelength band, and not absorbed by said sample such that transmission of the fourth wavelength band changes with variations in the optical throughout efficiency of the system,
wherein the fourth wavelength band is emitted by the source, modulated by the device, impinges upon the waveguide sample cell and the sample us detected by the detector.

14. The system according to claim 1, further comprising a source monitor detector disposed between the source and the waveguide cell,
wherein a portion of the electromagnetic radiation at the first and second wavelength bands emitted by the source impinge upon the source monitor detector to correct for variations in an intensity of the electromagnetic radiation emitted by the source at the first and second wavelength bands.

15. The system according to claim 1, further comprising:
at least one infrared transparent window;
an inlet valve formed from plastic;
inlet tubing formed from plastic;
an outlet valve formed from plastic; and
outlet tubing formed from plastic,
wherein the window is arranged such that the first and second wavelength bands of electromagnetic radiation emitted by the source impinge upon the window prior to entering the waveguide sample cell, and
wherein the inlet valve, inlet tubing, outlet valve and outlet tubing are arranged such that the sample can be input to the waveguide cell and output from the waveguide cell connecting tubing and inlet and outlet fittings, the system being constructed and arranged such that the waveguide cell can be used as a disposable item.

16. A system for monitoring relative concentrations of a chemical species, the system comprising:
a sample including first and second isotopic forms of the chemical species;
a source emitting a broad band of electromagnetic radiation including first and second wavelength bands, the first wavelength band corresponding to an absorption band of the first isotope, the second wavelength band corresponding to an absorption band of the second isotope;
first and second filters for filtering the broad band of radiation emitted by the source to define the first and second wavelength bands;
a device for modulating the first and second wavelength bands of radiation emitted by the source;
a waveguide cell defining a sample cell and having a pathlength of from about 30 centimeters to about 100 centimeters and an inner diameter of from about 0.3 millimeters to about 2.0 millimeters; and
a detector for detecting electromagnetic radiation at the first and second wavelengths,
wherein the system is arranged such that electromagnetic radiation emitted by the source is modulated by the device and filtered by the filters, impinges upon the sample, and at least 10% of the first and second wavelengths of electromagnetic radiation that enters the waveguide cell passes through the waveguide cell and impinges upon the detector.

17. The system according to claim 16, wherein the waveguide cell transmits at least about 20% of the first and second wavelength bands of electromagnetic radiation incident upon the waveguide cell.

18. The system according to claim 16, wherein the source is formed from first and second light emitting diodes, the first light emitting diode being emits electromagnetic radiation at the first wavelength band, the second light emitting diode being emits electromagnetic radiation at the second wavelength band.

19. The system according to claim 16, wherein the sample is a sample of human breath the first isotopic form is $^{12}CO_2$ and the second isotopic form is $^{13}CO_2$.

20. The system according to claim 19, wherein the waveguide cell is a hollow glass fiber waveguide cell.

21. A method of measuring relative concentrations of a sample including first and second isotopic forms, the method comprising the steps of:
simultaneously emitting electromagnetic radiation at first and second wavelength bands;

modulating the first and second wavelength bands of electromagnetic radiation;

impinging at least a portion of the modulated first and second wavelengths of electromagnetic radiation upon the sample, the first wavelength band corresponding to an absorption band of the first isotopic form, the second wavelength band corresponding to an absorption band of the second isotopic form, the sample being contained within a waveguide cell having a pathlength of from about 30 centimeters to about 100 centimeters and an inner diameter of from about 0.3 millimeters to about 2.0 millimeters and transmitting at least about 10% of the first wavelength band and the second wavelength band of the portion of the electromagnetic radiation that entered the waveguide; and measuring absorption of the modulated electromagnetic radiation at the first and second wavelength bands by the first and second isotopic forms of the chemical species, respectively.

22. The method according to claim 21, wherein the impinging step includes impinging the radiation upon a sample of human breath, and wherein the first isotopic form is $^{12}CO_2$ and the second isotopic form is $^{13}CO_2$.

23. The method according to claim 22, wherein the impinging step includes impinging the radiation upon a sample contained within a hollow glass fiber waveguide cell.

24. The method according to claim 21, wherein the impinging step includes impinging the radiation upon a sample contained within a hollow glass fiber waveguide cell.

25. The method according to claim 21, wherein the emitting step includes simultaneously emitting a third wavelength band of electromagnetic radiation, the third wavelength band being between the first and second wavelength bands, the first and second isotopic forms being incapable of absorbing the third wavelength band such that the third wavelength band can be used to monitor variations in an optical throughput efficiency of the system.

26. The method according to claim 25, further comprising the step of modulating the first, second and third wavelengths.

27. A system for monitoring relative concentrations of a chemical species, the system comprising:

a sample including first and second isotopic forms of the chemical species;

an electromagnetic radiation source emitting first and second wavelength bands, the first wavelength band corresponding to an absorption band of the first isotopic form, the second wavelength band corresponding to an absorption band of the second isotopic form;

a device for modulating the electromagnetic radiation emitted by the source at the first and second wavelength bands;

a waveguide defining a sample cell, said waveguide having a first window at one end and a second window at the opposite end and a pathlength from about 30 cm to about 100 cm; and a detector, wherein the system is arranged such that at least a portion of the electromagnetic radiation emitted by the source is modulated by the device, enters the waveguide through said first window, impinges upon the sample contained within the waveguide cell, at at least 10% of the first and second wavelength bands of electromagnetic radiation that enters the waveguide is transmitted through the waveguide sample cell and said second window and impinges upon the detector.

28. The system according to claim 27, wherein the system is arranged such that at least about 30% of the first and second wavelength bands of electromagnetic radiation that enters the wave guide is transmitted through the waveguide.

29. The system according to claim 27, wherein the waveguide cell has an inner diameter of from about 0.3 millimeters to about 2.0 millimeters.

30. The system according to claim 27, wherein the source is a broad band source, and wherein the system further comprises filters to define the first and second wavelength bands.

31. The system according to claim 27, wherein the detector includes a Fourier transform infrared spectrometer.

32. The system according to claim 27, wherein the source is formed from first and second light emitting diodes, the first light emitting diode emitting electromagnetic radiation at the first wavelength band, and the second light emitting diode emitting electromagnetic radiation at the second wavelength band.

33. The system according to claim 32, wherein the source further includes a third light emitting diode, the third light emitting diode emitting electromagnetic radiation at a third wavelength band located between the first and second wavelength bands, and wherein the system further comprises a source monitor detector disposed between the source and the waveguide cell, and wherein a portion of the electromagnetic radiation at the first, second and third wavelength bands emitted by the source impinge upon the source monitor detector to correct for variations in an intensity of the electromagnetic radiation emitted by the source at the first, second and third wavelength bands.

34. The system according to claim 27, wherein the sample is a sample of human breath, the first isotopic form is $^{12}CO_2$ and the second isotopic form is $^{13}CO_2$.

35. The system according to claim 27, wherein the source emits a third wavelength band of electromagnetic radiation, the third wavelength band being between the first and second wavelength bands, and not absorbed by said first and second isotopic forms such that transmission of the third wavelength band changes with variations in an optical throughput efficiency of the system, wherein the third wavelength band is emitted by the source, modulated by the device, impinges upon the waveguide sample cell and the sample and is detected by the detector.

36. The system according to claim 35, further comprising a source monitor detector disposed between the source and the waveguide cell, wherein a portion of the electromagnetic radiation at the first, second and third wavelength bands emitted by the source impinge upon the source monitor detector to correct for variations in an intensity of the electromagnetic radiation emitted by the source at the first, second and third wavelength bands.

37. The system according to claim 35, wherein the source emits a fourth wavelength band, a distance between the third wavelength band and the first wavelength band being less than a distance between the fourth wavelength band and the first wavelength band, a distance between the fourth wavelength band and the second wavelength band being less than a distance the third wavelength band and the second wavelength band, and not absorbed by said first and second isotopic forms such that the fourth wavelength band changes with variations in the optical throughput efficiency of the system, wherein the fourth wavelength band is emitted by the source, modulated by the device, impinges upon the waveguide sample cell and the sample and is detected by the detector.

38. The system according to claim 27, further comprising a source monitor detector disposed between the source and the waveguide cell, wherein a portion of the electromagnetic radiation at the first and second wavelength bands emitted by the source impinge upon the source monitor detector to correct for variations in an intensity of the electromagnetic radiation emitted by the source at the first and second wavelength bands.

39. The system according to claim 27, further comprising:

at least one infrared transparent window;

an inlet valve formed from plastic;

inlet tubing formed from plastic;

an outlet valve formed from plastic; and outlet tubing formed from plastic, wherein the window is arranged such that the first and second wavelength bands of electromagnetic radiation emitted by the source impinge upon the window prior to entering the waveguide sample cell, and wherein the inlet valve, inlet tubing, outlet valve and outlet tubing are arranged such that the sample can be input to the waveguide cell and output from the waveguide cell connecting tubing and inlet and outlet fittings, the system being constructed and arranged such that the waveguide cell can be used as a disposable item.

40. A system for monitoring relative concentrations of a chemical species, the system comprising:

a sample including first and second isotopic forms of the chemical species;

an electromagnetic radiation source, said source emitting broad band electromagnetic radiation including first and second wavelength bands, the first wavelength band corresponding to an absorption band of the first isotope, the second wavelength band corresponding to an absorption band of the second isotope;

a first bandpass filter, passing a wavelength band corresponding to said first wavelength band;

a second bandpass filter, passing a wavelength band corresponding to said second wavelength band;

a device for modulating the first and second wavelength bands of radiation emitted by the source;

a waveguide, said waveguide having a path length of about 30 cm to about 100 cm; and a detector;

wherein the system is arranged such that at least a portion of electromagnetic radiation emitted by the source is modulated by the device and filtered by the filters, then enters the waveguide and impinges upon the sample, and at least 10% of the first wavelength and second wavelength of the portion of the electromagnetic radiation entering the waveguide are transmitted through the waveguide cell and impinges upon the detector.

41. A method of measuring relative concentrations of a sample including first and second isotopic forms, the method comprising the steps of:

introducing said sample into a waveguide sample cell having a pathlength of about 30 cm to about 100 cm;

simultaneously emitting electromagnetic radiation at first and second wavelength bands;

modulating the first and second wavelength bands of electromagnetic radiation;

impinging at least a portion of the modulated first and second wavelengths of electromagnetic radiation upon the sample in said waveguide sample cell, the first wavelength band corresponding to an absorption band of the first isotopic form, the second wavelength band corresponding to an absorption band of the second isotopic form; and measuring absorption of the modulated electromagnetic radiation at the first and second wavelength bands by the first and second isotopic forms of the chemical species, respectively.

* * * * *